United States Patent [19]

Hess et al.

[11] Patent Number: 5,346,480
[45] Date of Patent: Sep. 13, 1994

[54] SYRINGE WITH RETRACTABLE NEEDLE

[75] Inventors: Charles D. Hess; Charles W. Wickstrom, both of Tulsa, Okla.

[73] Assignee: Q-Med, Inc., Tulsa, Okla.

[21] Appl. No.: 990,669

[22] Filed: Dec. 14, 1992

[51] Int. Cl.[5] ............................................. A61M 5/32
[52] U.S. Cl. ................................... 604/197; 604/198; 604/218
[58] Field of Search ............... 604/110, 187, 188, 192, 604/195, 197, 198, 218, 263, 221–222, 224, 229; 128/919

[56] References Cited

U.S. PATENT DOCUMENTS

| | | | |
|---|---|---|---|
| 3,890,971 | 6/1975 | Lesson et al. | 604/110 |
| 4,994,034 | 2/1991 | Botich et al. | 604/110 |
| 4,998,920 | 3/1991 | Johnson | 604/198 |
| 4,998,924 | 12/1991 | Ranford | 604/198 |
| 5,000,736 | 3/1991 | Kaufhold, Jr. et al. | 604/110 |
| 5,017,187 | 5/1991 | Sullivan | 604/110 |
| 5,019,043 | 5/1991 | Segui Pastor et al. | 604/110 |
| 5,019,044 | 5/1991 | Tsao | 604/110 |
| 5,024,660 | 6/1991 | McNaughton | 604/110 |
| 5,026,353 | 6/1991 | Bartman | 604/192 |
| 5,026,354 | 6/1991 | Kocses | 604/195 |
| 5,030,208 | 7/1991 | Novacek et al. | 604/195 |
| 5,049,133 | 9/1991 | Villen Pascual | 604/110 |
| 5,053,018 | 10/1991 | Talonn et al. | 604/198 |
| 5,057,087 | 10/1991 | Harmon | 604/198 |
| 5,061,251 | 10/1991 | Juhasz | 604/198 |
| 5,064,419 | 11/1991 | Gaarde | 604/195 |
| 5,066,277 | 11/1991 | Carrell et al. | 604/110 |
| 5,066,280 | 11/1991 | Braithwaite | 604/110 |
| 5,066,281 | 11/1991 | Stevenson-Michener | 604/110 |
| 5,067,942 | 11/1991 | Jaffe et al. | 604/110 |
| 5,106,379 | 4/1992 | Leap | 604/198 |
| 5,158,549 | 10/1992 | McCarthy | 604/110 |
| 5,169,392 | 12/1992 | Ranford et al. | 604/198 |

FOREIGN PATENT DOCUMENTS 8902759 4/1989 PCT Int'l Appl. ................. 604/218

*Primary Examiner*—C. Fred Rosenbaum
*Assistant Examiner*—V. Alexander

[57] ABSTRACT

A syringe comprising a barrel having a needle extending from a needle end of the barrel, a plunger and a protective sleeve. There is a groove in the inner surface of the sleeve and a key extending from the outer surface of the barrel into the groove. The groove has a longitudinal section and a circumferential section. The circumferential section has opposing and offset zig-zag edges. A spring biases the barrel toward the protective sleeve. By pressing the plunger against the force of the spring, the key moves in the groove, sliding along the zig-zag edges. The design of the groove cooperates with the operation of the syringe and can cause the key to move into the longitudinal groove and the needle to thereby retract into the protective sleeve after the plunger is depressed.

21 Claims, 4 Drawing Sheets

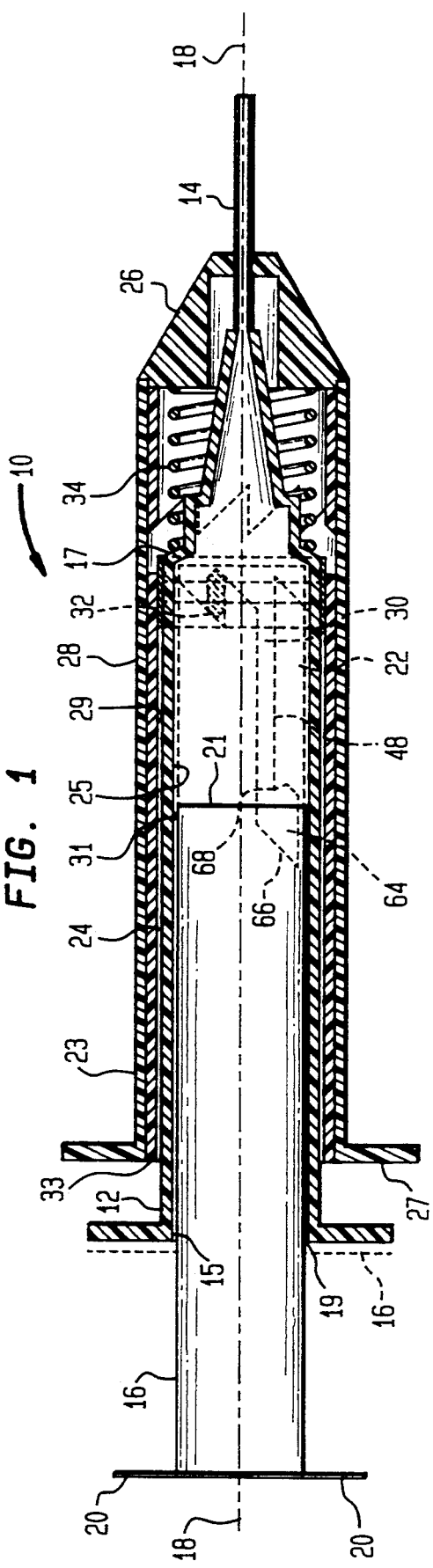
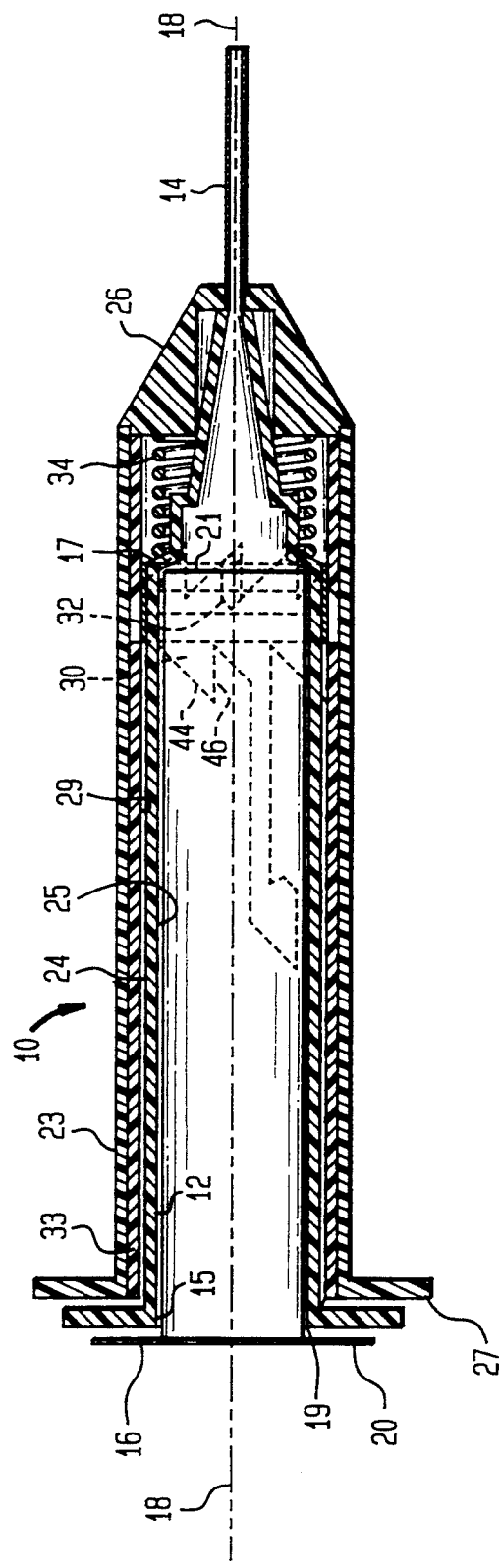

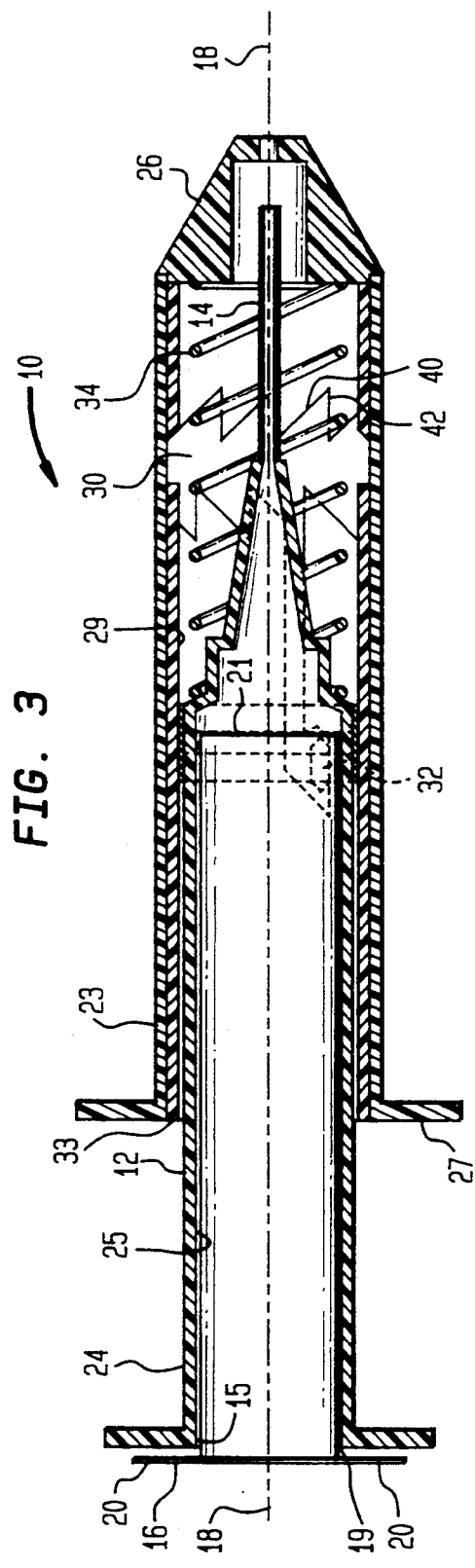

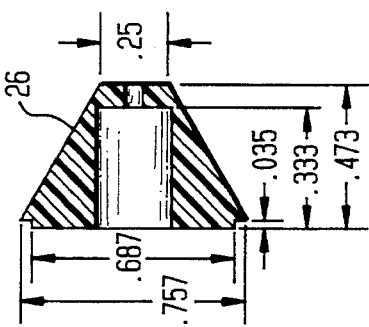
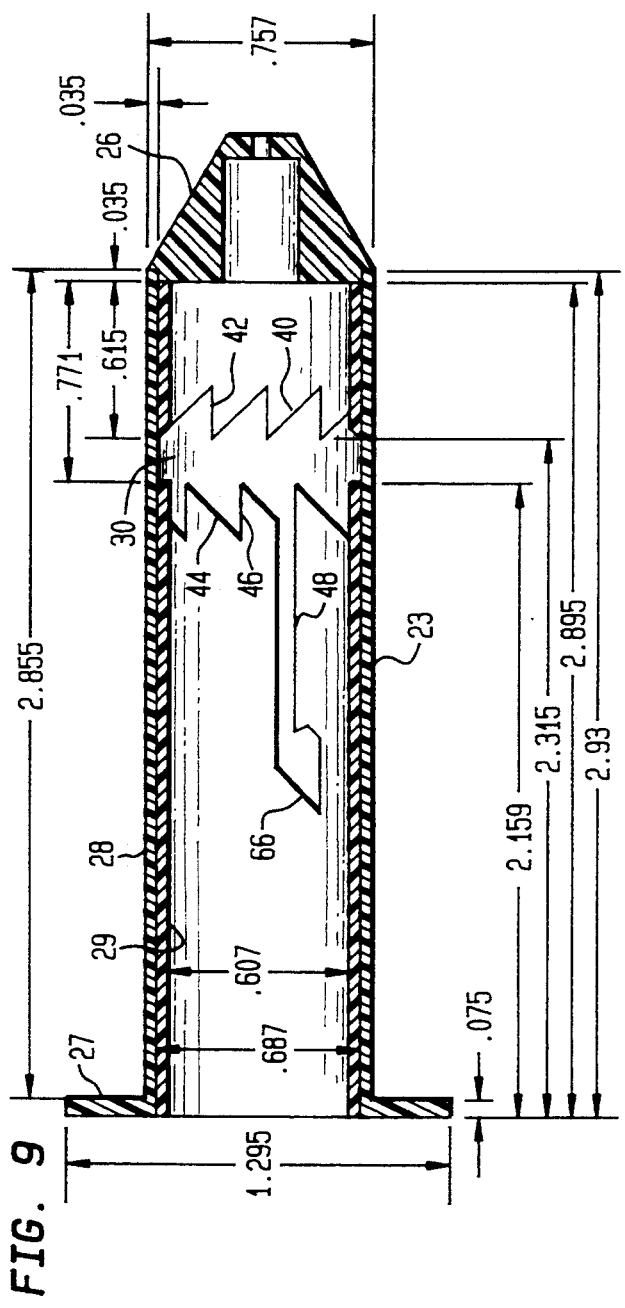
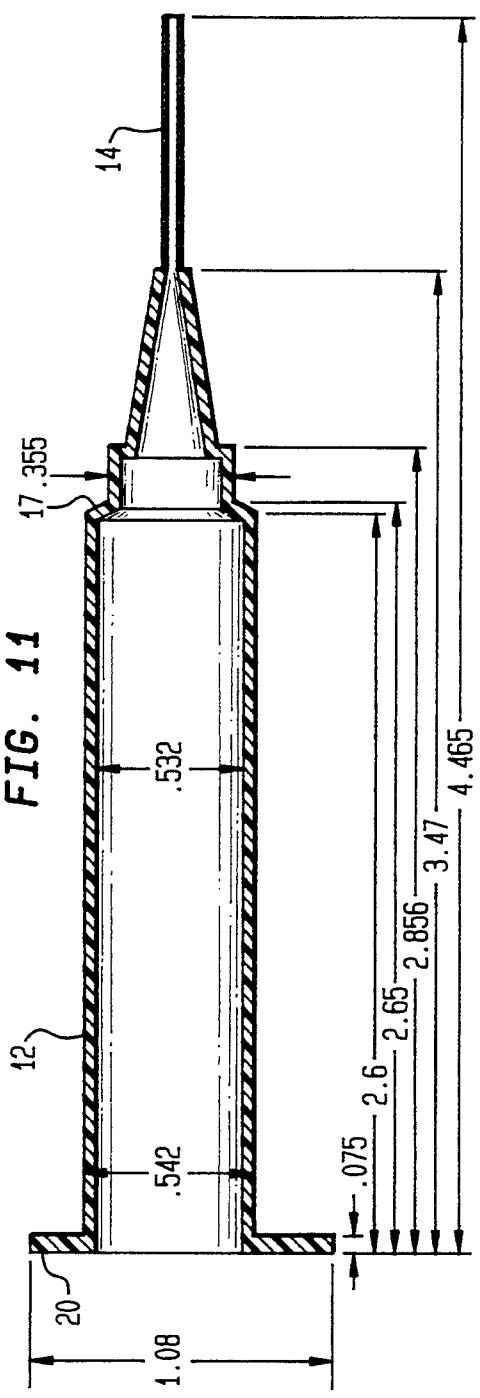

SYRINGE WITH RETRACTABLE NEEDLE

BACKGROUND OF THE INVENTION

1. Field of the Invention

The present invention relates to hypodermic syringes, and more particularly, to a hypodermic syringe with a needle which retracts into a protective sleeve, and a related method.

2. Description of Related Art

Hypodermic syringes having a variety of designs to shield the needle after use are disclosed in the art. Various shields are disclosed, as well as syringes having needle assemblies which retract into an outer sleeve also referred to as a shield or sheath. Syringes are also disclosed having needles which retract into the syringe barrel or plunger.

A syringe is disclosed in U.S. Pat. No. 5,106,379 which comprises a cylindrical syringe barrel having a needle secured at one end. A plunger is slidingly received within the interior barrel chamber. A boss extendes radially outward from the cylindrical syringe barrel. There is sheath slidingly positioned on the cylindrical syringe barrel. The sheath is movable between a retracted needle exposing position and an extended needle surrounding position. The sheath has a slot to receive the boss. The slot includes a longitudinal portion extending parallel to the axis of the syringe barrel and a laterally extending portion extending laterally with respect to the cylindrical syringe barrel. The laterally extending protion is on the end of the groove opposite the needle. A spring biasingly urges the sheath toward the extended needle surrounding position. The spring is secured to the cylindrical syringe barrel and the sheath such that the spring biasingly rotates the boss into a laterally extending portion of the slot as the sheath is advanced to the extended needle surrounding position. When the boss is positioned in the laterally extending portion of the slot the sheath cannot be retracted due to the axial forces acting on the sheath. There is a restraining means for selectively restraining the sheath in the needle exposing position. A restraining means is disclosed to be a barb attached to the cylindrical syringe barrel. The sheath includes a barb receiving aperture such that when the sheath is advanced to the needle exposing position the barb receiving aperture captures the barb so as to prevent the sheath from being advanced to the extended needle surrounding position. A release means selectively releases the sheath from the restraining means to allow the spring to advance the sheath to the extended needle surrounding position. A trigger is secured to the sheath and can be used to move the barb receiving aperture away from the barb such that the barb does not prevent the spring from biasingly urging the sheath to the extended needle surrounding position.

U.S. Pat. No. 5,024,660 discloses a syringe having a barrel with a needle mounted on one end. A piston is mounted for movement longitudinally within the barrel. There is a tubular sleeve dimensioned to fit over the barrel. A longitudinal groove is along the outside of the barrel. The groove has lateral extensions at both ends. The sleeve has an internal projection which extends into the groove. The sleeve can be locked in to a retracted position or an extended position. The syringe is operated by hand with no automatic feature to cause the sleeve to extend around and shield the needle.

U.S. Pat. No. 5,061,251 discloses a syringe having a movable shield between a first position for shielding a needle and a second position for shielding the needle member. There is a means for manually moving the shield member from the first to the second position. A spring means normally biases the shield member in the shielding position.

U.S. Pat. No. 5,057,087 discloses a syringe barrel, a needle extending from the barrel, a needle extending from the barrel, a movable safety sleeve surrounding the barrel, and a sleeve cap to cover the forward end of the sleeve. The syringe barrel includes a forward detent, an intermediate detent, and a rear detent. The safety sleeve also includes an inner ring for selective engagement with the detents. The safety sleeve is axially movable on the syringe barrel from an initial transport position on the intermediate detent, to a retracted position on the rear detent to expose the needle, and to a locked safety position on the forward detent. The sleeve cap is held on the safety sleeve by friction when the sleeve is in the transport position, and by positive engagement with the safety sleeve when the sleeve is in the locked safety position.

U.S. Pat. Nos. 4,998,920 and 5,066,277 discloses syringes where the needle is located in a protective sleeve after use.

A continuing goal in the art is automatic retraction of the needle into a protected position. Many attempts have been made to retract the needle using a spring including those disclosed in U.S. Pat. Nos. 4,994,034; 5,000,736; 5,017,187; 5,019,044; 5,026,353; 5,049,133 and 5,064,419.

Other patents of interest disclosing syringes with retractable needles include U.S. Pat. Nos. 5,019,043; 5,026,354; 5,030,208 and 5,066,280. Patents of interest which disclose single use needles include U.S. Pat. Nos. 5,066,281 and 5,067,942.

Generally, the art discloses that there has been a continuing interest to develop a syringe which has a needle that can be retracted to prevent accidental needle pricks to the patients and to persons administering injections. Given the circumstances surrounding injections and needle disposal it desireable for the needle to automatically retract. Preferably, there should be a minimum of additional steps to cause needle retraction by the person administering the injection. Such an improvement is desireable for syringes contemplated for single or multiple uses.

SUMMARY OF THE INVENTION

The present invention is a syringe comprising a barrel, a plunger and a protective sleeve. The syringe is controlled solely through the plunger. Upon completion of an injection there is an automatic retraction means interconnected between the barrel and outer protective sleeve to automatically retract the needle without the application of any additional hand or finger manipulation by the person administering the injection.

The present invention is an improved syringe. The syringe comprises, in combination, a barrel having a needle at one end, a plunger disposed to be inserted in the barrel opposite the needle, and a longitudinal axis. The barrel, needle and plunger all are coaxial to the longitudinal axis of the syringe.

The barrel has a barrel circumference, a plunger end, a needle end, an outer surface, and an inner surface. The plunger end defines a plunger opening. A needle means extends from the needle end of the barrel, preferably coaxial to the syringe. The plunger has a compression end and a needle end. The needle end of the plunger extends longitudinally into the barrel through the open plunger end of the barrel. There is a liquid reservoir between the needle end of the plunger and the needle end of the barrel.

The syringe further comprises a sleeve in which the barrel extends. The sleeve has a sleeve circumference, a needle end through which the needle can extend, and an open plunger end through which the barrel extends into the sleeve. The needle end of the barrel is disposed in the sleeve with the needle directed toward the sleeve needle end. The barrel has a barrel outer surface and the sleeve has a sleeve inner surface which are interconnected by a groove in one of said surfaces and a key extending from the opposing surface.

The syringe will be described with respect to a preferred embodiment where there is a slot or groove, and most preferably a groove in the sleeve inner surface. Alternatively, there can be a slot through the sleeve wall. The groove has at least one longitudinal groove section which extends longitudinally for at least part of the sleeve length, and a circumferential section which extends circumferentially for at least part of the sleeve circumference. The circumferential section of the groove is preferably located at the needle side end of the groove. The circumferential section of the sleeve groove has a needle side edge and a plunger end side edge.

In a preferred groove the circumferential extension has a needle side edge having at least two needle side slide edges extending toward the needle end at an angle to the longitudinal axis. Each needle side edge extends from the sleeve groove and ends at a needle side stop. Each succeeding needle side slide edge begins at the stop of the previous needle side slide edge.

A plunger side edge of the circumferential section of the circumferential has at least one plunger side slide edge. Each plunger side slide edge extends toward the plunger end at an angle to the longitudinal axis. The plunger side slide edges extend from the barrel groove and end at a plunger side stop. Each succeeding plunger side slide edge begins at the stop of the previous plunger side slide edge.

Each plunger side slide edge extends from the circumferential section toward the plunger end and each needle side slide edge extends from the groove toward the needle end along the circumferential length of the sleeve groove. Opposing needle side edges and plunger side slide edges are staggered in the circumferential direction whereby a longitudinal projection from a stop on one of the needle side or plunger side edge intersects a slide edge of the opposite side edge. Opposing plunger and needle side slide edges extend toward the circumferential section around the sleeve circumference.

The inner surface of the sleeve further defines at least one longitudinal groove section, with each longitudinal groove section extending from a plunger side slide edge toward the sleeve plunger end. There is at least one, and preferably two longitudinal grooves. There can be three, four or more longitudinal grooves. At least one of the longitudinal groove sections can have a means to lock the key when the needle is retracted. The longitudinal groove sections can extend from adjacent plunger side slide edges, but preferably extend from alternate plunger side slide edges. There can be more than two plunger side slide edges between longitudinal grooves. There can be one assembly groove extending from the groove circumferential extension to the sleeve plunger end.

A key, which preferably, can rotate circumferentially around the barrel, extends from the barrel outer surface. When the barrel is disposed in the sleeve, the key fits into the groove. The key in the groove limits the longitudinal travel of the barrel, and the needle in the sleeve. There is a means for the key to move around the outer barrel circumference in the sleeve groove.

There is a biasing means, such as spring, preferably a coil spring, located to bias the needle into the sleeve, toward the sleeve plunger end and into the sleeve. The geometry of the groove enables the needle to be locked in a position to extend beyond the sleeve needle end to be used as a conventional syringe. Upon depression of the plunger the key interacts with the groove to enable the biasing means to force the needle to retract into sleeve. Optionally, there can be means to lock the needle into the retracted position, either permanently for one shot uses, or for reuse upon unlocking the barrel.

The present invention includes a method of operation of the above described syringe. In accordance with the method of the present invention, the syringe can be used to inject fluid and retract the needle solely through compression on the piston. Therefore, the injection can be made and the needle automatically retracted merely by pushing in on the plunger.

The present invention includes a conversion kit having a key assembly which can be attached to a conventional syringe and used in combination with the sleeve of the present invention.

BRIEF DESCRIPTION OF THE DRAWINGS

FIG. 1 is a partial sectional view of a preferred embodiment of the syringe of the present invention with the needle in the extended position prior to injection.

FIG. 2 is a view of the assembly of FIG. 1 immediately after the piston has been moved toward the needle for an injection, and then the sleeve unlocked.

FIG. 3 is a view of the assembly of FIG. 1 with the needle in a retracted position.

FIG. 4 is a projection showing the groove on the inner surface of the sleeve of a preferred embodiment of the present invention.

FIG. 5 is a sectional edge view of a means to mount the key on the outside surface of the syringe barrel.

FIG. 6 is an edge view of the key assembly shown in FIG. 5.

FIG. 7 is a top view of the element shown in FIG. 5.

FIG. 9 is a view of the sleeve shown in FIG. 1 showing the dimensions (in inches) useful for a 5 cubic centimeter syringe.

FIG. 10 is a view showing the dimensions (in inches) of the needle end of the sleeve shown in FIG. 9.

FIG. 11 is a view of the barrel shown in FIG. 1 showing the dimensions (in inches) useful for a 5 cubic cenimeter syringe.

DESCRIPTION OF THE PREFERRED EMBODIMENTS

Figure 8:
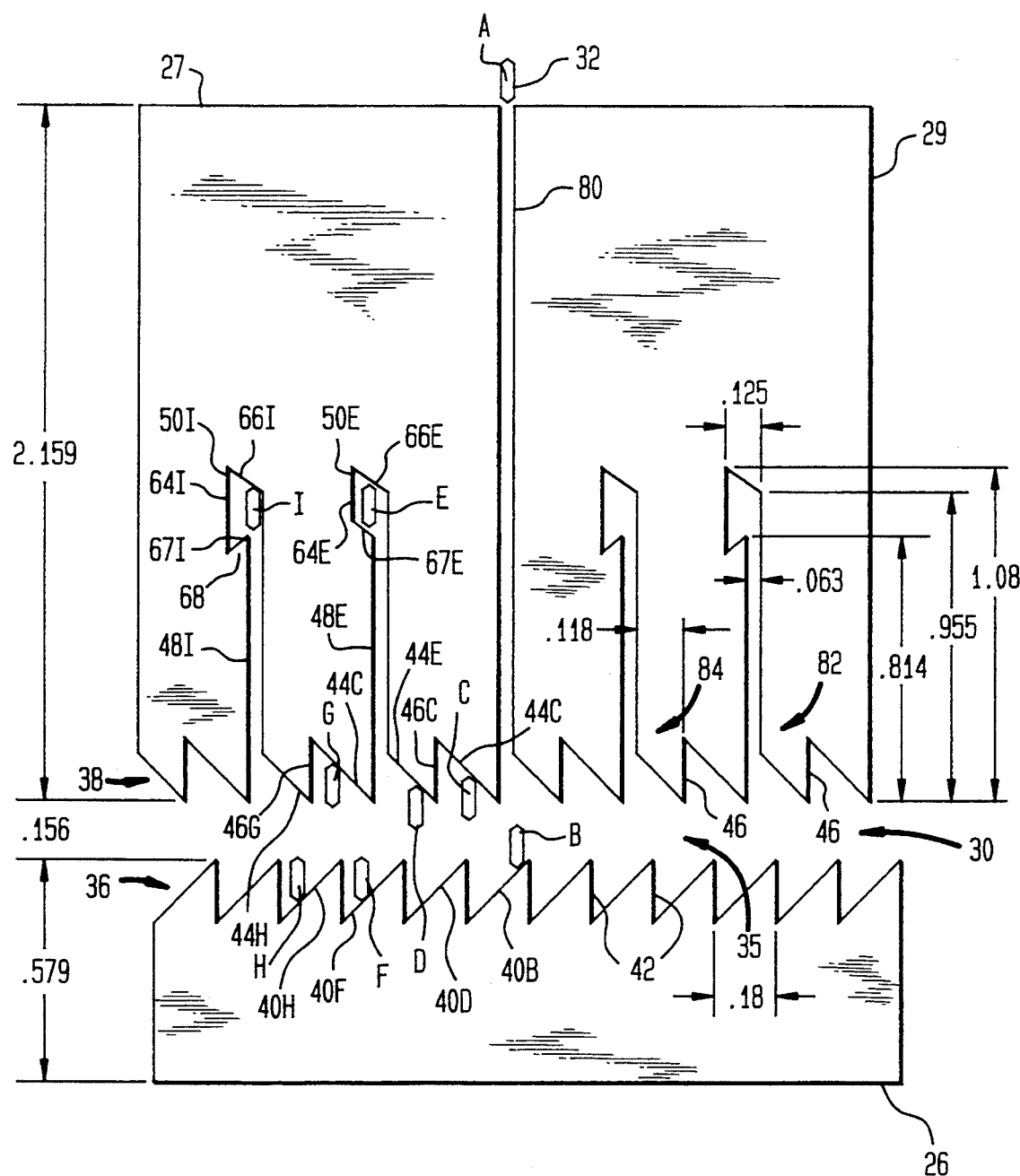
FIG. 8 is another view as in FIG. 4, used to illustrate operation of the present invention and showing dimensions (in inches) useful for a 5 cubic centimeter syringe.

The present invention is an improved syringe which will be understood by those skilled in the art by reference to FIGS. 1–11 which illustrate a preferred embodiment. In this preferred embodiment the syringe comprises a barrel, a plunger and a protective sleeve. There is a groove on the inner surface of the sleeve and a key extending from the outer surface of the barrel into the groove. The travel of the key in the groove controls the operation of the syringe. It is recognized that the groove can be on the outer surface of the barrel with the key extending from the inner surface of the barrel.

The syringe 10 comprises, in combination, a barrel 12, a needle 14 extending from barrel 12, and a plunger 16 disposed to be inserted into the barrel 12 opposite the needle 14. The barrel 12, needle 14 and plunger 16 all are coaxial to the longitudinal axis 18 of the syringe 10.

The barrel 12 has a barrel circumference, a plunger end 15, a barrel needle end 17, a barrel outer surface 24, and a barrel inner surface 25. The barrel plunger end 15 defines a plunger opening 19. The needle means 14 extends from the needle end 17 of the barrel 12 coaxial to the syringe 10. The needle can be a hollow needle of the type know in the art which can be assembled with the barrel 12. The tip of the needle is open to allow communication from outside of the barrel 12 into a reservoir in the barrel 12.

The plunger 16 has a compression end 20 and a needle end 21. The needle end 21 can extend longitudinally into the open plunger end 15 of the barrel 12. There is a liquid reservoir 22 between the needle end 21 of the plunger 15 and the needle end 17 of the barrel 12. There is a seal 31 between the outer surface of plunger 16 and barrel inner surface 25. The seal can be a conventional seal used between a syringe barrel and plunger. A useful seal is an O-ring syringe type seal 31 secured around the outer surface of the plunger 16. Preferably, this seal has two circumferential extensions from the plunger outer surface which wipe against the inner surface of the barrel 12.

The syringe 10 further comprises a sleeve 23 in which the barrel 12 is inserted. Sleeve 23 has a sleeve plunger end 27, sleeve needle end 26, a sleeve circumference, sleeve inner surface 29, sleeve outer surface 28, and a longitudinal axis coaxial with syringe axis 18. The sleeve 23 has a needle end 26 and an open plunger end 27. The needle end 17 of barrel 12 is disposed in the sleeve 23 with the needle 14 directed toward the sleeve needle end 26. The barrel 12 has a barrel outer surface 24 and the sleeve 23 has a sleeve inner surface 29 which are interconnected by a combination of a slot or groove in either the barrel outer surface or the seeve inner surface, and a key extending into the groove from the opposing surface. Preferably, there is a groove 30 in the sleeve inner surface 29. The sleeve 23 can be a single unit in which there is a slot or groove 30. Preferably, the sleeve 23 comprises an inner layer 33. Groove 30 can be formed as a slot in layer 33 which in turn forms the grooved inner surface 29 of sleeve 23.

At least a section of groove 30 extends for a portion of the longitudinal distance between the sleeve needle end 26 and the sleeve plunger end 27 and at least a section of groove 30 extends circumferentially. A key 32 extends from the barrel outer surface 24. When the barrel 12 is disposed in the sleeve 23, the key 32 fits into the groove 30. As will be discussed, the key 32 in groove 30 limits the longitudinal and circumferential travel of the barrel 12 and needle 14 relative to the sleeve 23.

There is a biasing means, such as spring 34, located to bias the needle 14 toward the sleeve plunger end 27 and into the sleeve 23. Prior to use the syringe 10 can have the needle 14 retracted into the sleeve 23, or it can be in an extended position. The geometry of the groove 30 enables the needle 14 to be locked into a position where it extends beyond the sleeve needle end 26 to be used as a conventional syringe. Upon depression of the plunger 16 the key 32 interacts with the groove 30 to enable the biasing means to force the needle 14 to retract into sleeve 23. The key 32 travels in the longitudinal groove toward the sleeve plunger end 27. Optionally, there can be means to lock the needle 14 into the retracted position, either permanently for one shot uses, or for reuse upon unlocking the barrel 12.

Referring to FIGS. 1–4 and 8, sleeve groove 30 is in sleeve inner surface 26 and has a needle side circumferential extension section 35 which extends circumferentially for at least part of the sleeve circumference. In the preferred embodiment circumferential extension 35 extends for substantially the full circumference of the inner surface 29 of sleeve 23. Sleeve groove extension 35 has a needle side edge 36 and a plunger end side edge 38. The needle side edge 36 has at least two needle side slide edges 40 extending toward the needle end 26 at an angle to the longitudinal axis 18. Each edge 40 extends from the sleeve circumferential groove section 36 and ends at a needle side stop 42. The succeeding needle side slide edge 40 begins at the stop 42 of the previous needle side slide edge 40. The perimeter of the needle side edge 36 is preferably a saw tooth shape as shown. Preferably, each saw tooth has the same longitudinal and circumferential length.

The plunger side edge 38 has at least one and preferably two plunger side slide edges 44 extending toward the plunger end 27 at an angle to the longitudinal axis 18. Each edge 44 extends from the sleeve circumferential groove 30 and ends at a plunger side stop 46. The succeeding plunger side slide edge 44 begins at the stop 46 of the previous plunger side slide edge 44. As with the needle side, the perimeter of plunger side edge 38 is preferably a saw tooth shape having teeth with the same longitudinal and circumferential lenths.

Each plunger side slide edge 44 extends from section 35 of groove 30 toward the plunger end 27 and each needle side slide edge 40 extends toward the needle end 26 along the circumferential groove extension 35 of the sleeve groove 30. Opposing needle side slide edges 40 and plunger side slide edges 44 are staggered in the circumferential direction (i.e., offset zigzags). The needle side stops 42 and plunger side stops 46 are preferably paralled to longitudinal axis 18. The needle side slide edges 40 are at an angle to axis 18 and preferably intersect the needle side end of stop 42 at an acute angle. Each plunger side slide edge 44 is at an angle to axis 18 and preferably intersects the plunger end of stop 46 at an acute angle. Each needle side edge 40 is at an angle opposite that of plunger side slide edge 44. Stated another way, it needle side slide edges 40 and adjacent stops form an "S", than plunger side slide edges 44 and adjacent stops form a "Z", and vica versa. The opposing saw tooth configurations of the needle and plunger side edges are staggered so that the stop on one side (i.e., the needle side slide edge stop) is longitudinally opposite a side slide edge of the opposite side (i.e., the plunger side slide edge). A longitudinal projection from a stop (i.e., 42 or 46) on one of the needle side or plunger side slide edges (i.e., 40 or 44) intersects a slide edge of the opposite side edge.

The inner surface 29 of the sleeve has at least one longitudinal groove section 48. Each longitudinal groove section 48 extends from a plunger side slide edge 44 of the circumferential sleeve groove section 35 toward the plunger end 27. A lock means is preferably located at at least one plunger end 50 of longitudianl groove section 48 to lock the needle 14 in a retracted position.

Key 32 can extend from the barrel outer surface 24 at the barrel plunger end 17 into the sleeve groove 30. There is preferably key assembly 54 (FIGS. 5, 6 and 7) to enable the key to move around the barrel outer circumference. Referring to FIG. 5, the key assembly comprises the key 32 interlocked in a channel 39 in key ring 37. Key ring 37 is attached to the barrel outer surface 24. The key 32 can move circumferentially in channel 39.

Biasing means, preferably spring 34, and more preferably a coil spring is located to force the barrel 12 longitudinally away from the sleeve needle end 26. The spring 34 is preferably located between the needle end 17 of the barrel 12 and the sleeve needle end 26 inside the sleeve 23. In this way the spring 34 can move the needle without contacting the fluid in the reservoir 22.

In a preferred and specific embodiment of the syringe 10, the longitudinal groove 30 has a plunger side end circumferential extension 64. The plunger side end cirumferential extension 64 is longer in the longitudinal direction than the key 32 and extends circumferentially for a distance greater than the circumferential width of the key. The plunger side extension has a plunger side slide edge 66 which can extend at an angle to the longitudinal axis toward the plunger end 22 of the sleeve. In a specific embodiment at least one circumferential extension can have a notch 68 at the needle side of the extension. This notch 68 locks the key in extension 64 and thereby the needle 14 in a retracted position to prevent the needle from extending even when pressure is applied to the plunger.

FIGS. 6 to 11 show dimensions, in inches, for the key assembly 54, ring 37, barrel 12, plunger 16 and sleeve 23 for a preferred 5 cubic centimeter syrings. A preferred coil spring has an outer diameter of about 0.490 inches and a length of about 1.469 inches. The spring should have sufficient spring force in a compressed condition to drive the barrel until the key reaches the end of the longitudinal groove section.

The operation of a specific and preferred embodiment is illustrated with reference to FIGS. 1-4 and 8. The sleeve 23 has key ring 37 attached near the barrel needle end. Key 32 extends from the key ring 37. The key 32 can rotate circumferentially around the barrel circumference in key groove 30.

Referring to FIG. 8, the barrel 12 is inserted into the sleeve 23. Key 32 at position A fits into longitudinal assembly groove 80. The barrel 12 slides into sleeve 23 toward sleeve needle end 26. The barrel 12 intercepts spring 34 and is forced against the spring 34 until key 32 intercepts needle side slide edge 40B at position B. The key 32 slides down slide edge 40B while circumferentially rotating in channel 39. The barrel does not rotate. The key 32 is stopped at needle side stop at position B. Upon release of the force on barrel plunger end 15, spring 34 forces the key 32 to position C at plunger side slide edge 44C. The key 34 slides up plunger side slide edge 44C, while circumferentially rotating in channel 39. The key 34 stops at plunger side stop 46 at position C. At this point the syringe 10 is in a needle extended position such as shown in FIG. 1. Plunger 16 can be in a drawn or inserted position (phantom lines in FIG. 1). The syringe 10 can be used as a conventional syringe.

For various uses, such as shipment, the syringe 10 is preferably in a retracted position such as shown in FIG. 3. By compressing the barrel plunger end 15, preferably through the use of the plunger 16, the barrel 12 is forced against spring 34 until the key 32 intercepts needle side slide edge 40D at position D. The key slides along slide edge 40D until it reaches needle side stop 42 at position D. Upon release of the force on barrel plunger end 15, spring 34 forces the key 32 to plunger side slide edge 44E. The key 34 slides up plunger side slide edge 44E, while circumferentially rotating in channel 39. The key 32 intercepts and slides into longitudinal groove section 48E. Spring 34 forces the barrel 12 and key 32 to groove plunger end 50E. The plunger end 50E of the groove section 48E can have a plunger side circumferential extension 64E. The key 34 can slide along plunger side slide edge 66E into circumferential extension 64E. In this way the needle is retracted, and the plunger can be in an inserted or retracted position.

To put the needle 14 in an extended position, the barrel plunger end 15, preferably through the use of the plunger 16, is compressed to force the barrel 12 against spring 34 until the key 32 intercepts needle side slide edge 67E of circumferential extension section 64. The key slides along edge 67E and back down longitudinal groove 48E to position F where key 32 intercepts needle side slide edge 40F at position F. The key slides along slide edge 40F until it reaches needle side stop 42 at position F. Upon release of the force on barrel plunger end 15, spring 34 forces the key 32 to plunger side slide edge 44G. The key 34 slides up plunger side slide edge 44G, while circumferentially rotating in channel 39. The key 32 intercepts and is stopped at plunger side stop 46G. The needle 14 is locked in an extended position and the syringe 10 is configured as shown in FIG. 1 and can be used as a conventional syringe for at least one injection.

FIGS. 2, 3 and 8 illustrate the use of the syringe with the key in position G for a one shot injection where the needle is locked in a retracted position after the injection. Upon forcing plunger 16 in, barrel 12 is forced toward the needle end and against spring 34. The key 32 moves from the stop 46G to position H. The key 32 intercepts needle side slide edge 40H at position H. The key slides along slide edge 40H until it reaches needle side stop 42 at position H. Upon release of the force on barrel plunger end 15, spring 34 forces the key 32 to plunger side slide edge 44H. The key 34 slides up plunger side slide edge 44H, while circumferentially rotating in channel 39. The key 32 intercepts and slides into longitudinal groove section 48I. Spring 34 forces the barrel 12 and key 32 to groove plunger end 50I. The plunger end 50I of the groove section 48I can have a plunger side circumferential extension 64. The key 34 can slide along plunger side slide edge 66I into circumferential extension 64I. In this way the needle is retracted. This method of needle extension and retraction can be repeated around the sleeve in groove assemblies such as in groove assemblies 80 and 82.

In a preferred embodiment there is a means to lock the needle in a retracted position even after only one injection. This can be done by a suitable locking means. A useful and preferred locking means is to simply have a notch extension 68 on the longitudinal groove side of slide 67I. Pressure on the barrel 12 will force key 32 down slide 67I to intercept locking notch extension 68. This will prevent reuse of the needle.

The present invention can be applied to many existing syringes. An adjustable key ring 37 can be connected, or otherwise secured to the outside surface of a syring barrel. Suitable connecting means such as adhesives, set screws or the like can be used. Once this is done a mating sleeve can be assembled in the manner recited.

The invention has been described with reference to its preferred embodiments. From this description, a person of ordinary skill in the art may appreciate changes that could be made in the invention which do not depart from the scope and spirit of the invention as described above and claimed hereafter.

What is claimed is:

1. A syringe comprising:
   a longitudinal axis;
   a barrel having a barrel circumference, a needle end, an outer surface, and an inner surface, and a plunger end defining a plunger opening,
   a needle means extending from the needle end of the barrel;
   a plunger having a compression end and a needle end, with the needle end capable of being positioned to extend longitudinally into the plunger opening of the barrel, there being a reservoir in the barrel between the needle end of the plunger and the needle end of the barrel;
   a sleeve having an open sleeve plunger end with the barrel capable of being positioned to extend into the sleeve through the sleeve open end, a sleeve needle end, a sleeve circumference, an inner surface and an outer surface,
   a groove defined in the sleeve inner surface the groove having at least one longitudinal groove section which extends longitudinally for at least part of the sleeve length and a circumferential section which extends circumferentially for at least part of the sleeve circumference, the circumferential section having a needle side edge and a plunger end side edge,
   the needle side edge of the circumferential section having at least two needle side slide edges extending from the sleeve groove toward the needle end at an angle to the longitudinal axis and ending at a needle side stop, with the succeeding needle side slide edge beginning at the stop of the previous needle side slide edge,
   the plunger side edge of the circumferential section having at least one plunger side slide edge extending from the sleeve groove toward the plunger end at an angle to the longitudinal axis and ending at a plunger side stop, with each succeeding plunger side slide edge beginning at the stop of the previous plunger side slide edge, each plunger side slide edge, needle side slide edges and plunger side slide edges are located along the circumferential section in a staggered configuration whereby a longitudinal projection from a stop on one of the needle side or plunger side edge intersects a slide edge of an opposing side slide edge, opposing plunger side slide edges and needle side slide edges extending toward the circumferential section around the sleeve circumference,
   the inner surface of the sleeve further defining at least one longitudinal groove, with each longitudinal groove extending from a plunger side slide edge to a lock means;
   a key extending from the side of the barrel at the plunger end, into the sleeve groove, and
   a means to force the barrel longitudinally away from the sleeve needle end.

2. The syringe of claim 1 wherein each needle side stop extends longitudinally from the needle side slide edge to the circumferential stop section, and each plunger side stop extends longitudinally from the plunger side slide edge to the circumferential section.

3. The syringe of claim 1 wherein the groove is a slot through the sleeve.

4. The syringe of claim 1 wherein the means to force the plunger longitudinally away from the barrel needle end is a spring located between the needle end of the barrel and the needle end of the sleeve.

5. The syringe of claim 4 wherein the spring is a coil spring around the needle end of the barrel.

6. The syringe of claim 1 wherein the longitudinal groove has a plunger side end circumferential extension, and the plunger side end has a slide edge which extends at an angle to the longitudinal axis toward the plunger end of the barrel.

7. The syringe of claim 6 wherein the circumferential extension has a notch at the needle side of the extension.

8. The syringe of claim 1 further comprising a means for the key to rotate around the outer barrel surface while in the sleeve groove.

9. The syringe of claim 8 wherein the means for the key to rotate is a key ring capable of being secured to the outer surface of the barrel and the key extends from the key ring having an outer surface and has a means to slide around the ring.

10. The syringe of claim 9 wherein the means for the key to slide around the key ring is a channel in the outer surface of the key ring.

11. An improved syringe of the type having a longitudinal axis; a barrel having a barrel circumference, a needle end, an outer surface, and an inner surface, and a plunger end defining a plunger opening, a needle means extending from the needle end of the barrel; plunger having a compression end and a needle end, with the needle end capable of being positioned to extend longitudinally into the plunger opening of the barrel, there being a reservoir in the barrel between the needle end of the plunger and the needle end of the barrel; the improvement comprising:
   a sleeve having an open sleeve plunger end with the barrel capable of being positioned to extend into the sleeve through the sleeve open end, a sleeve needle end, a sleeve circumference, an inner surface and an outer surface,
   a groove defined in the sleeve inner surface the groove having at least one longitudinal groove section which extends longitudinally for at least part of the sleeve length and a circumferential section which extends circumferentially for at least part of the sleeve circumference, the circumferential section having a needle side edge and a plunger end side edge,
   the needle side edge of the circumferential section having at least two needle side slide edges extending from the sleeve groove toward the needle end at an angle to the longitudinal axis and ending at a needle side stop, with the succeeding needle side slide edge beginning at the stop of the previous needle side slide edge,
   the plunger side edge of the circumferential section having at least one plunger side slide edge extending from the sleeve groove toward the plunger end at an angle to the longitudinal axis and ending at a plunger side stop, with each succeeding plunger side slide edge beginning at the stop of the previous plunger side slide edge, each plunger side slide edge, needle side slide edges and plunger side slide edges are located along the circumferential section in a staggered configuration whereby a longitudinal projection from a stop on one of the needle side or plunger side edge intersects a slide edge of an opposing side slide edge, opposing plunger side slide edges and needle side slide edges extending toward the circumferential section around the sleeve circumference, the inner surface of the sleeve further defining at least one longitudinal groove, with each longitudinal groove extending from a plunger side slide edge to a lock means;

a key extending from the side of the barrel at the plunger end, into the sleeve groove, and a means to force the barrel longitudinally away from the sleeve needle end.

12. The syringe of claim 11 further comprising a means for the key to rotate around the outer barrel surface while in the sleeve groove.

13. The syringe of claim 12 wherein the means for the key to rotate is a key ring capable of being secured to the outer surface of the barrel and the key extends from the key ring having an outer surface and has a means to slide around the ring.

14. The syringe of claim 13 wherein the means for the key to slide around the key ring is a channel in the outer surface of the key ring.

15. A syringe conversion kit for a syringe of the type comprising having a longitudinal axis; a barrel; a needle means extending from the barrel; a plunger barrel; the conversion kit comprising:

a sleeve having an open sleeve plunger end, a sleeve needle end, a sleeve circumference, an inner surface and an outer surface, a groove defined in the sleeve inner surface the groove having at least one longitudinal groove section which extends longitudinally for at least part of the sleeve length and a circumferential section which extends circumferentially for at least part of the sleeve circumference, the circumferential section having a needle side edge and a plunger end side edge, the needle side edge of the circumferential section having at least two needle side slide edges extending from the sleeve groove toward the needle end at an angle to the longitudinal axis and ending at a needle side stop, with the succeeding needle side slide edge beginning at the stop of the previous needle side slide edge, the plunger side edge of the circumferential section having at least one plunger side slide edge extending from the sleeve groove toward the plunger end at an angle to the longitudinal axis and ending at a plunger side stop, with each succeeding plunger side slide edge beginning at the stop of the previous plunger side slide edge, each plunger side slide edge, needle side slide edges and plunger side slide edges are located along the circumferential section in a staggered configuration whereby a longitudinal projection from a stop on one of the needle side or plunger side edge intersects a slide edge of an opposing side slide edge, opposing plunger side slide edges and needle side slide edges extending toward the circumferential section around the sleeve circumference, the inner surface of the sleeve further defining at least one longitudinal groove, with each longitudinal groove extending from a plunger side slide edge to a lock means;

a key extending from the side of the barrel at the plunger end, into the sleeve groove, and a means to force the barrel longitudinally away from the sleeve needle end.

16. The syringe conversion kit of claim 15 further comprising a means for the key to rotate around the outer barrel surface while in the sleeve groove.

17. The syringe conversion kit of claim 16 wherein the means for the key to rotate is a key ring capable of being secured to the outer surface of the barrel and the key extends from the key ring having an outer surface and has a means to slide around the ring.

18. The syringe conversion kit of claim 17 wherein the means for the key to slide around the key ring is a channel in the outer surface of the key ring.

19. A method of operating a syringe comprising the steps of:

withdrawing a plunger of a syringe having a barrel, from the barrel, the syringe further comprising:

a longitudinal axis;

the barrel having a barrel circumference, a needle end, an outer surface, and an inner surface, and a plunger end defining a plunger opening;

a needle means extending from the needle end of the barrel;

the plunger having a compression end and a needle end, with the needle end capable of being positioned to extend longitudinally into the plunger opening of the barrel, there being a reservoir in the barrel between the needle end of the plunger and the needle end of the barrel;

a sleeve having an open sleeve plunger end with the barrel capable of being positioned to extend into the sleeve through the sleeve open end, a sleeve needle end, a sleeve circumference, an inner surface and an outer surface;

a groove defined in the sleeve inner surface, the groove having at least one longitudinal groove section which extends longitudinally for at least part of the sleeve length and a circumferential section which extends circumferentially for at least part of the sleeve circumference, the circumferential section having a needle side edge and a plunger end side edge;

the needle side edge of the circumferential section having at least two needle side slide edges extending from the sleeve groove toward the needle end at an angle to the longitudinal axis and ending at a needle side stop, with the succeeding needle side slide edge beginning at the stop of the presious needle side slide edge;

the plunger side edge of the circumferential section having at least one plunger side slide edges extending from the sleeve groove toward the plunger end at an angle to the longitudinal axis and ending at a plunger side stop, with each succeeding plunger side slide edge beginning at the stop of the previous plunger side slide edge, each plunger side slide edge, needle side slide edges and plunger side slide edges are located along the circumferential section in a staggered configuration whereby a longitudinal projection from a stop on one of the needle side or plunger side edges intersects a slide edge of an opposing side slide edge, opposing plunger side slide edges and needle side slide edges extending toward the circumferential section around the sleeve circumference;

the inner surface of the sleeve further defining at least one longitudinal groove, with each longitudinal groove extending from a plunger side slide edge to a lock means, a key extending from the side of the barrel at the plunger end, into the sleeve groove; and a means to force the barrel longitudinally away from the sleeve needle end; the method further comprising;

compressing the plunger into the barrel, wherein plunger pushes the barrel toward the needle end until the key intersects a needle side slide edge of the circumferential section with the key rotating until the key intersects the needle side stop; and removing the compression force on the barrel to allow the means to force the plunger, to force the barrel away from the needle side of the circumferential section wherein the key intersects a plunger side slide edge which communicates with a longitudinal groove section causing the key to rotate and pass into the longitudinal groove section which in turn causes the needle to retract into the barrel.

20. The method of claim 19 further comprising locking the needle in the retracted position.

21. The method of claim 19 wherein the syringe further comprises a means for the key to rotate around the outer barrel circumference in the sleeve groove, and the method further comprises rotating the key as the plunger is withdrawn and compressed.

* * * * *